(12) United States Patent
Cabri et al.

(10) Patent No.: US 7,019,140 B2
(45) Date of Patent: Mar. 28, 2006

(54) PROCESS FOR THE SYNTHESIS OF PERGOLIDE

(75) Inventors: Walter Cabri, Rozzano (IT); Paolo Paissoni, Druento (IT); Jacopo Roletto, Turin (IT); Piera Fonte, Turin (IT); Sara Olmo, Turin (IT)

(73) Assignee: Antibioticos S.p.A., Rodano (IT)

( * ) Notice: Subject to any disclaimer, the term of this patent is extended or adjusted under 35 U.S.C. 154(b) by 0 days.

(21) Appl. No.: 10/507,620

(22) PCT Filed: Mar. 10, 2003

(86) PCT No.: PCT/EP03/02423

§ 371 (c)(1),
(2), (4) Date: Sep. 14, 2004

(87) PCT Pub. No.: WO03/078432

PCT Pub. Date: Sep. 25, 2003

(65) Prior Publication Data

US 2005/0124812 A1    Jun. 9, 2005

(30) Foreign Application Priority Data

Mar. 15, 2002 (IT) .......................... MI2002A0555
Oct. 8, 2002 (IT) .......................... MI2002A2133

(51) Int. Cl.
*C07D 457/02* (2006.01)
*C07D 457/04* (2006.01)

(52) U.S. Cl. .......................... 546/67; 546/69
(58) Field of Classification Search .................. 546/67, 546/69
See application file for complete search history.

(56) References Cited

U.S. PATENT DOCUMENTS

| 3,901,894 A | 8/1975 | Kornfeld et al. |
| 4,166,182 A | 8/1979 | Kornfeld et al. |
| 5,463,060 A * | 10/1995 | Misner .......................... 546/68 |

FOREIGN PATENT DOCUMENTS

| CZ | 287 962 B | 3/2001 |
| EP | 0 026 671 A | 4/1981 |
| EP | 0 571 202 A | 11/1993 |
| WO | WO 00 44748 A | 8/2000 |

* cited by examiner

*Primary Examiner*—Charanjit S. Aulakh
(74) *Attorney, Agent, or Firm*—Rothwell, Figg, Ernst & Manbeck, P.C.

(57) ABSTRACT

A process for the synthesis of pergolide (Formula (I)) (D-6-n-propyl-8βmethylmercaptomethylergo line) from acid 9,10-dihydrolysergic is herein disclosed. The process can be carried out without isolating most intermediates and is particularly convenient both from the yield and safety standpoint. Moreover, pergolide thereby obtained is highly pure and can be conveniently transformed into pergolide mesylate

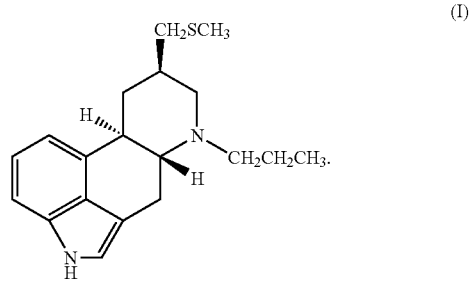

15 Claims, No Drawings

PROCESS FOR THE SYNTHESIS OF PERGOLIDE

CROSS REFERENCE TO RELATED APPLICATION

This application is a 35 USC § 371 National Phase Entry Application from PCT/EP2003/002423, filed Mar. 10, 2003, and designating the U.S.

FIELD OF THE INVENTION

The present invention relates in general to ergot alkaloids, in particular to a process for the synthesis of pergolide 1 from 9,10-dihydrolysergic acid.

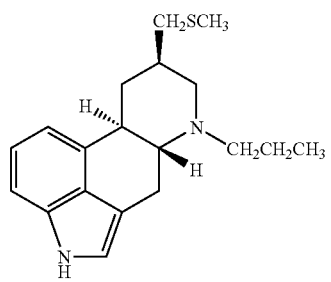

TECHNOLOGICAL BACKGROUND

Pergolide 1 (D-6-n-propyl-8β-methylmercaptomethylergoline) is a semisynthetic ergot alkaloid (produced by a fungus of genus *Claviceps, Claviceps purpurea*) used for the therapy of Parkinson's disease.

In particular, pergolide mesylate 2, a strong agonist of dopaminergic receptors, is used in therapy.

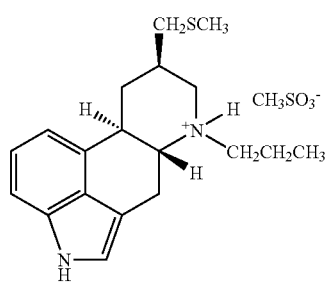

The usual starting product for the synthesis of pergolide is lysergic acid 3 (D-6-methyl-8β-carboxy-9-ergolene), which can be obtained by fermentation.

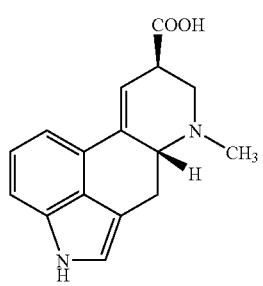

U.S. Pat. No. 4,166,182 discloses a synthesis of pergolide (scheme 1) which comprises conversion of lysergic acid into D-6-n-propyl-8β-hydroxymethylergoline 4, derivatization of the hydroxy group with methanesulfonyl chloride and reaction with sodium thiomethoxide. The resulting pergolide can then be salified with methanesulfonic acid.

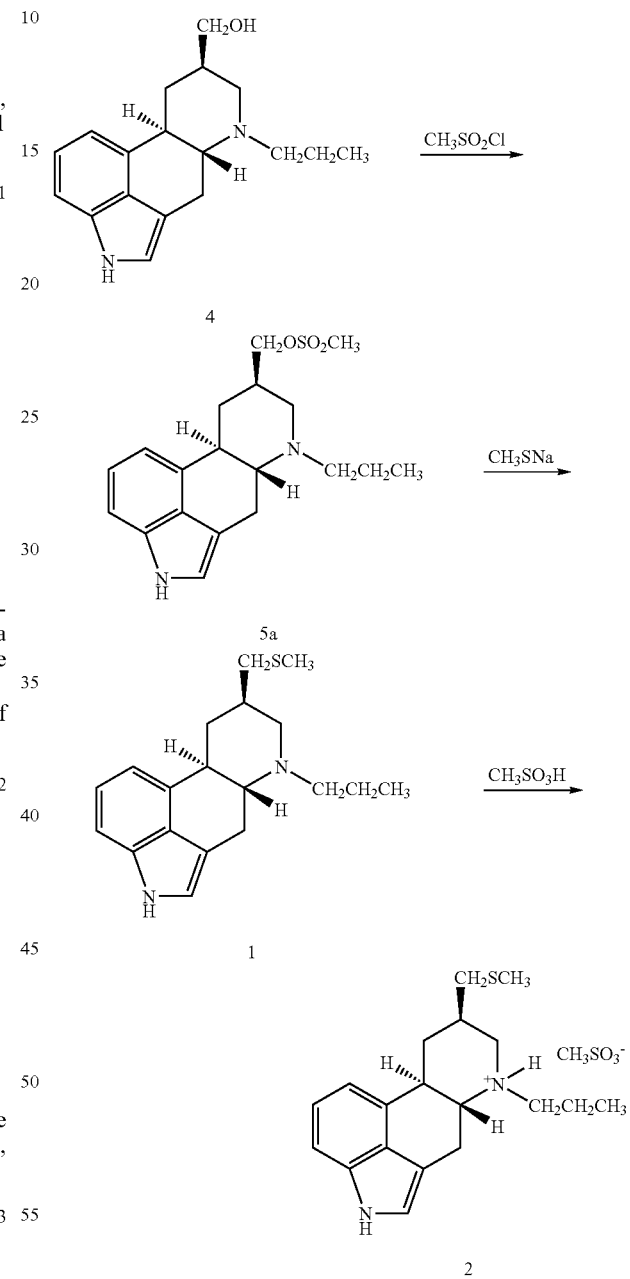

Compound 4 is obtained (scheme 2) by catalytic reduction of lysergic acid 3 to 9,10-dihydrolysergic acid 6, esterification of the acidic function and reduction of ester 7 with NaBH₄. The resulting compound 8, known as dihydrolysergol or 8,9-dihydroelimoclavine, is demethylated at the nitrogen in position 6 (following, for example, the procedure disclosed in U.S. Pat. No. 3,901,894 or the procedure disclosed in J. Pharm. Sci. 1981, 70, 1319–21), to give D-8β-hydroxymethylergoline 9, which is alkylated, for example, with propyl iodide in the presence of bases.

The key-intermediate of this pathway, dihydrolysergol 8, can also be obtained from elimoclavine, another fermentation product of *Claviceps purpurea*, by means of catalytic reduction, according to U.S. Pat. No. 3,901,894.

Scheme 2

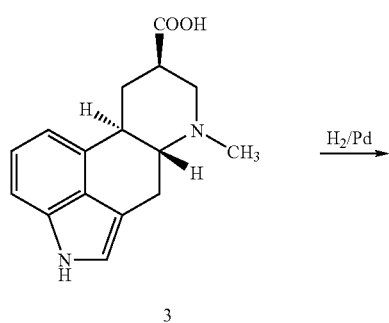

3

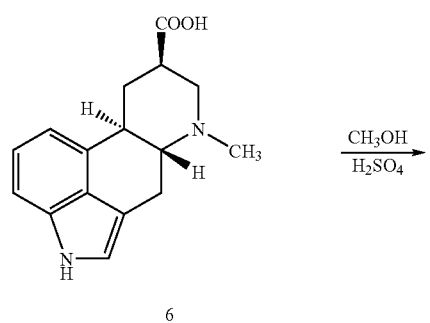

6

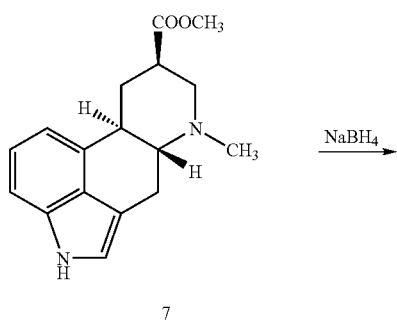

7

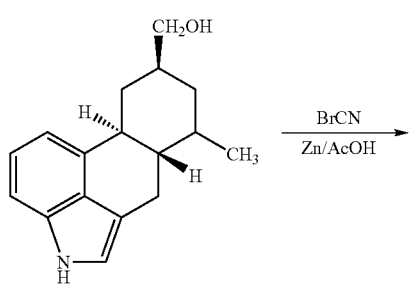

8

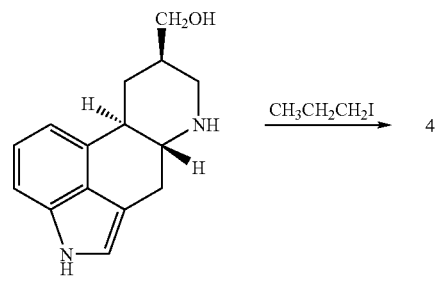

9

Alternatively, compound 4 can be obtained (scheme 3) by demethylation of ester 7 (obtained as described above) and by acylating with propionyl chloride the nitrogen in position 6; the treatment of compound 11 with LiAlH$_4$, which at the same time reduces the ester and the amidic function, affords compound 4.

Scheme 3

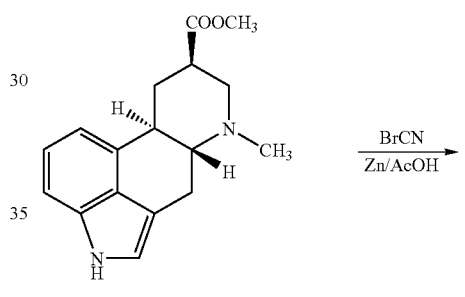

7

10

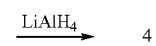

11

Even though these synthetic approaches allow to obtain highly pure pergolide, they require recovery of a number of intermediates, which determines poor yields (not higher than 20%) and makes the processes time-consuming and unsafe.

A more convenient synthesis in terms of yields has been disclosed by Misner in U.S. Pat. No. 5,465,060; the method allows to prepare "one-pot" pergolide from dihydrolysergol 8 (scheme 4), by demethylation of quaternary ammonium salts with nucleophiles, according to Hutchins e Duc (J. Org. Chem. 1973, 38, 1961–2). Dihydrolysergol 8 is transformed into an intermediate quaternary ammonium salt 12 by treatment with propyl iodide, whose alcoholic hydroxy group is subsequently derivatized with methanesulfonyl chloride to give an intermediate of formula 13. The treatment with sodium thiomethoxide allows at the same time demethylation of the quaternary nitrogen and formation of the thiomethyl ether. Despite a reduced number of steps and high yields (above 70%), the resulting pergolide is contaminated by some ergolinic impurities, which cannot be removed by conventional crystallization. For this reason two chromatographic purification steps are necessary, one of them with preparative HPLC [W. Misner et al., *Org. Process Res. Dev.* (1997) 1, 77–80], which require the use of highly toxic solvents, such as acetonitrile and chloroform [J. H. Kennedy, *Org. Process Res. Dev.* (1997) 1, 68–71] and increase the risk of exposure to the final product.

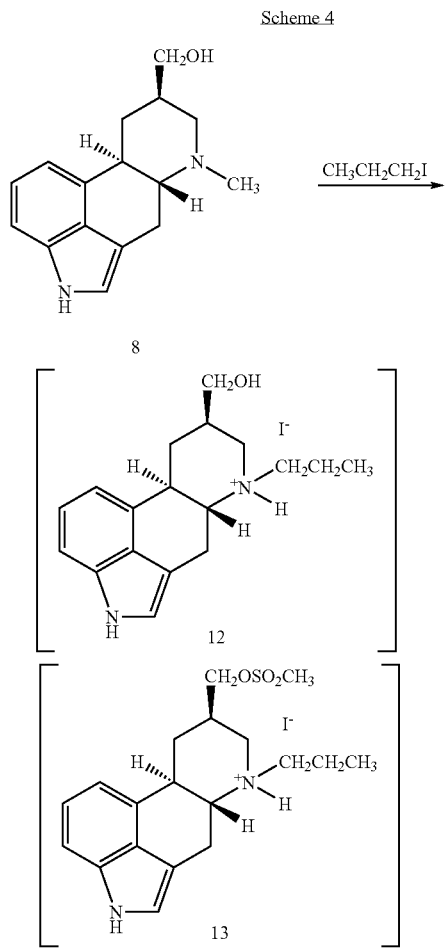

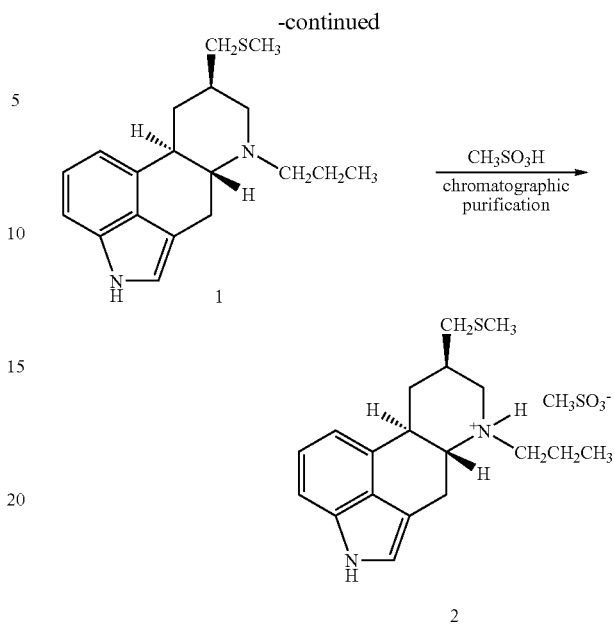

DETAILED DISCLOSURE OF THE INVENTION

It has now been found that the demethylation of quaternary ammonium salts with nucleophiles can be conveniently exploited for the synthesis of pergolide via intermediate 4 from 9,10-dihydrolysergic 6 acid.

The process of the present invention (scheme 5) comprises the following steps:

a) reaction of 9,10-dihydrolysergic acid 6 with propyl iodide to give D-6-methyl-6-n-propyl-8 B-propyloxycarbonyl-6-ergolinium iodide 14;

b) reduction of intermediate 14 to give D-6-methyl-6-n-propyl-8β-hydroxymethyl-6-ergolinium iodide 12;

c) demethylation of intermediate 12 with nucleophiles to give D-6-n-propyl-8β-hydroxymethylergoline 4;

d) reaction of intermediate 4 with alkylsulfonyl halides or toluenesulfonyl halides to give D-6-n-propyl-8β-alkylsulfonyloxymethylergoline or D-6-n-propyl-8β-tosyloxymethylergoline 5;

e) reaction of compound 5 with sodium thiomethoxide to give pergolide 1.

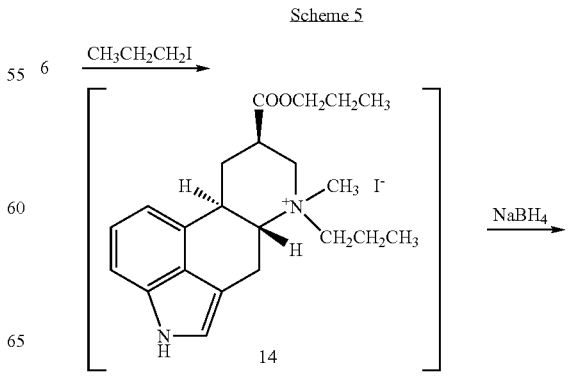

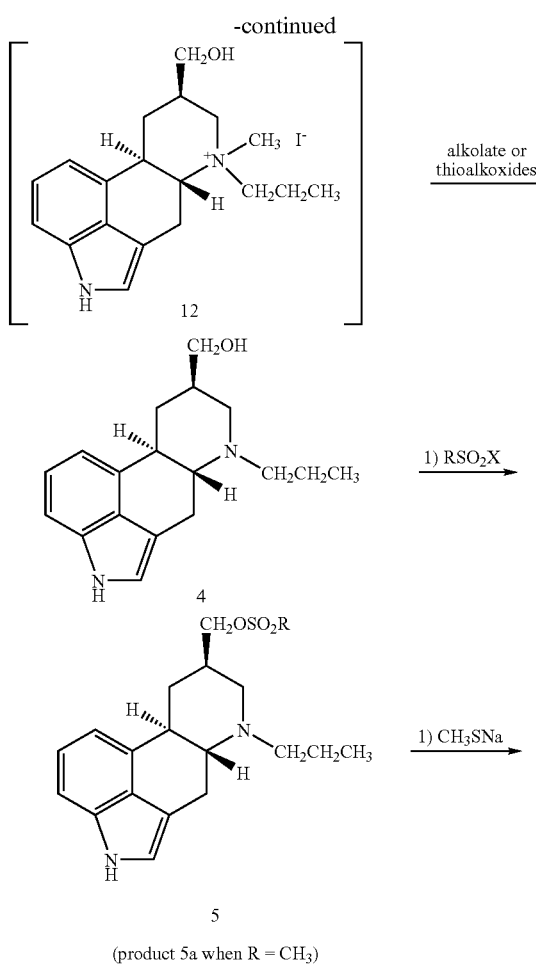

(product 5a when R = CH₃)

The reduction reaction is carried out according to conventional methods, preferably using metal hydrides, more preferably sodium borohydride.

The nucleophiles used for the demethylation of the salt of formula 12 are alkaline thioalkoxides, preferably sodium, lithium or potassium thioalkoxides; more preferably the demethylating agent is sodium thiomethoxide or sodium 2-mercaptoethoxide.

The alkylsulfonyl halides and the toluenesulfonyl halides have the formula RSO₂X, in which R is a straight or branched $C_1$–$C_3$ alkyl chain, or the group $C_6H_5CH_2$—, whereas X is a halogen selected from fluorine, chlorine, bromine, iodine. According to a preferred embodiment of the invention, the alkylsulfonyl halide is methanesulfonyl chloride.

Pergolide obtained according to the present invention can be conveniently transformed into pergolide mesylate according to known methods.

Intermediate 14 is a novel compound and is also object of the present invention.

Method A

According to a first preferred embodiment of the invention the process is carried out as follows.

Step a

Tipically 9,10-dihydrolysergic acid 6 is reacted with 3.2–6.0 equivalents of 1-iodopropane, preferably 4–5 equivalents, in the presence of a base, until complete conversion of the starting product into D-6-methyl-6-n-propyl-8β-propyloxycarbonyl-6-ergolinium iodide 14. The reaction is carried out at 60–90° C., preferably at 75–80° C., in a solvent selected from N-methylpyrrolidone, hexamethylphosphoramide, dimethylpropyleneurea and dimethylethyleneurea. 2.5–10 Volumes of solvent are used, preferably 4–5 volumes, with respect to the weight amount of 9,10-dihydrolysergic acid. The base is preferably an inorganic base, more preferably bicarbonate or carbonate anions, in an amount preferably ranging from 2.5 to 3.0 equivalents.

The reaction can be monitored by HPLC, using a C18 silica column, eluted with a phosphate buffer-acetonitrile mixture. After completion of the reaction (generally the conversion is complete within 10–12 hours at 75° C.) the solution of the salt 14 is cooled to room temperature and diluted with a solvent selected from N-methylpyrrolidone, hexamethylphosphoramide, dimethylpropyleneurea and dimethylethyleneurea. Preferably, 1–5 volumes of solvent are used (with respect to the final volume of the reaction mixture), more preferably 2–3 volumes.

Step b

The solution from step a) is heated to 25–50° C., preferably to 30–40° C., and the synthesis is continued by adding 0.5–3.5 equivalents, preferably 1.0–2.0 equivalents, of alkaline-earth ions, such as calcium or magnesium, and 6–16 equivalents, preferably 8–10 equivalents, of a reducing agent, preferably sodium borohydride (in both cases the amount is referred to the starting 9,10-dihydrolysergic acid). The mixture is reacted at 40–50° C., preferably at 45° C., until complete conversion of intermediate 14 into salt 12.

Step c

The demethylation of salt 12 is carried out by adding 5–20 equivalents, preferably 10–12 equivalents, of a nucleophile agent as defined above, preferably sodium thiomethoxide in a commercial 21% aqueous or methanolic solution. The reaction mixture is kept at 60–90° C., preferably at 70–80° C., until disappearance of ammonium salt 12. During the reaction, the water or methanol deriving from the commercial sodium thiomethoxide solution evaporate. Once the reaction is complete, if a commercial 21% methanolic sodium thiomethoxide solution has been used, the mixture is concentrated until complete removal of the methanol and the residue is taken up with the same volume of water as that before evaporation, then 0.2–1.0 volumes of an organic solvent and again one volume of water are added. The organic solvent is an ester, preferably methyl isobutyl ketone, ethyl acetate or n-butyl acetate, or a halogenated organic solvent, preferably methylene chloride. According to a particularly preferred embodiment of the invention the solvent is ethyl acetate. The mixture is stirred for 15–20 minutes at room temperature and the phases are separated. The aqueous phase is extracted with one volume of the same organic solvent and the two phases are separated. The organic phases are pooled, washed twice with one volume of water and concentrated to 1/10–1/20 of the starting volume. 0.2–1 Volumes (with respect to the volume before the concentration) of solvent are added and the mixture is concentrated again to 1/10–1/20 of the starting volume. Addition and concentration are repeated once, then a solvent selected from pyridine, picoline, lutidine in an amount ranging from 5 to 8 volumes, preferably from 6 to 7 volumes, is added.

Step d

After cooling to a temperature ranging from −10° C. to 50° C., preferably from −10° C. to 0° C., an alkylsulfonyl halide, preferably methanesulfonyl chloride, or a toluenesulfonyl halide, in an amount ranging from 1.0 to 3.0 equivalents, preferably from 1.5 to 2.0 equivalents (with respect to the starting 9,10-dihydrolysergic acid) is slowly dropped to the mixture from step c), under inert atmosphere. The mixture is reacted until complete disappearance of D-6-n-propyl-8β-hydroxymethylergoline 4. After completion of the reaction compound 5 is precipitated by addition of 0.2–0.8 volumes of 15% ammonium hydroxide and 1–3 volumes of water; the product is filtered and dried under vacuum at 40–70° C. for 10–30 hours. Compound 5 has a 97.5–98.0% purity; in the case of compound 5a, for example, the main impurity is D-6-methyl-8β-mesyloxymethylergoline (HPLC percentage area: 2.0–2.5%).

Compound 5 is further purified according to conventional chromatographic techniques. Compound 5 is dissolved in 8–12 volumes of mixtures of two organic solvents selected from alcohols and organic halogenated solvents, preferably methanol/dichloromethane.

More preferably, compound 5 is not essiccated, but dried by means of dissolution in 10–20 volumes of a halogenated organic solvent, preferably dichloromethane, followed by evaporation. The solvent is repeatedly added and evaporated, until the water in the solution amounts to less than 0.5%. The product is dissolved in a mixture of two organic solvents selected from alcohols and halogenated organic solvents, preferably methanol/dichloromethane. The solution is adsorbed on 10–100 volumes of normal phase silica, then eluted with organic solvents selected from esters, methyl isobutyl ketone, ethyl acetate or n-butyl acetate, preferably ethyl acetate, alcohols, methanol, ethanol, isopropanol, preferably methanol and organic halogenated solvents, preferably dichloromethane, and binary and ternary mixtures thereof. Other solvents known in the literature can also be used. The fractions containing pure compound 5 are pooled and concentrated to 1/10–1/20 volume; a solvent selected from N-methylpyrrolidone, hexamethylphosphoramide, dimethylpropyleneurea and dimethylethyleneurea, in an amount ranging from 10 to 50 volumes, preferably 20–30 volumes, with respect to compound 5, is added and the solution is further concentrated to remove the residues of the solvents used in the purification.

Step e

The solution from step c) is added with 5–20 equivalents, preferably 10–12 equivalents, of sodium thiomethoxide in commercial 21% methanolic solution, at a temperature ranging from 0° C. to 80° C., preferably from 20 to 30° C., and the solution is concentrated under vacuum to distil methanol off. The reaction is monitored by HPLC until complete disappearance of compound 5. After completion of the reaction (30–60' at 25° C.), 1–3 volumes of water (with respect to the starting volume of the synthesis of the pergolide) are added and complete precipitation of pergolide 1 is observed with negligible losses in the mother liquors. The product is dried at 40–70° C. for 10–30 hours.

Method B

According to a second, even more preferred embodiment of the invention (hereinafter referred to as "method B"), steps a)–e) are carried out as follows.

Step a

Tipically 9,10-dihydrolysergic acid 6 is reacted with 3.2–6.0 equivalents of 1-iodopropane, preferably 4–5 equivalents, in the presence of a base, until complete conversion of the starting product into D-6-methyl-6-n-propyl-8β-propyloxycarbonyl-6-ergolinium iodide 14. The reaction is carried out at 60–90° C., preferably at 75–80° C., in a solvent selected from N-methylpyrrolidone, hexamethylphosphoramide, dimethylpropyleneurea and dimethylethyleneurea. 2.5–10 Volumes of solvent are used, preferably 4–5 volumes, with respect to the weight amount of 9,10-dihydrolysergic acid. The base is preferably an inorganic base, more preferably bicarbonate or carbonate anions, in an amount preferably ranging from 2.5 to 3.0 equivalents.

The reaction can be monitored by HPLC, using a C18 silica column, eluted with a phosphate buffer-acetonitrile mixture. Generally the conversion is complete within 10–12 hours at 75° C.

Step b

The solution from step a) is heated to 25–65° C., preferably to 45–60° C., and the synthesis is continued by adding 0.5–3.5 equivalents, preferably 1.0–2.0 equivalents, of alkaline-earth ions, such as calcium or magnesium, and 2–10 equivalents, preferably 3–5 equivalents, of a reducing agent, preferably sodium borohydride (in both cases the amount is referred to the starting 9,10-dihydrolysergic acid) dissolved in 1–5 volumes, preferably 2–3 volumes (with respect to the initial amount of 9,10-dihydrolysergic acid) of a solvent selected from N-methylpyrrolidone, hexamethylphosphoramide, dimethylpropyleneurea and dimethylethyleneurea. The mixture is reacted at 45–60° C., preferably at 55° C., until complete conversion of intermediate 14 into salt 12.

Step c

The reaction mixture from step b) is added with 5–20 equivalents, preferably 14–16 equivalents, of an inorganic strong base, preferably sodium hydroxide, and is added with 5–20 equivalents, preferably 14–16 equivalents, of a nucleophile as defined above, preferably with commercial 2-mercaptoethanol. The mixture is kept at 60–90° C., preferably at 65–75° C., until disappearance of the salt 12. After completion of the reaction compound 4 is recovered by crystallization from an EDTA aqueous solution and an alkaline or alkaline-earth metal chloride aqueous solution, preferably a KCl or NaCl aqueous solution, most preferably a NaCl aqueous solution. More precisely, the reaction mixture is added of 0.1–0.5 volumes (with respect to the volume of the reaction mixture) of methanol, 1–3 volumes, preferably 1.5–2.5 volumes, of an EDTA aqueous solution at a concentration of 20–100 g/l, preferably 40–60 g/l, adjusted to pH 10–14, preferably to pH 12–13, with an inorganic base as defined above, 1–3 volumes, preferably 1.5–2.5 volumes, of an NaCl aqueous solution at a concentration of 200–350 g/l, keeping the temperature at 60–90° C., preferably at 65–75° C. The mixture is subsequently cooled down to 0–25° C., preferably to 5–10° C. The product is filtered and washed with an EDTA aqueous solution at a concentration of 20–100 g/l, preferably 40–60 g/l, adjusted to pH 10–14, preferably to pH 12–13, with an inorganic base as defined above, and subsequently washed with deionized water. Compound 4 has a 98.5–99.0% purity; the main impurity is compound 8 (HPLC percentage area: 0.8–1.3%). The humid product is dissolved in 20–50 volumes (with respect to the product's volume), preferably 30–40 volumes, of an organic ester solvent, preferably methyl isobutyl ketone, ethyl acetate or n-butyl acetate, or an organic halogenated solvent, preferably methylene chloride. More preferably, the solvent is ethyl acetate. The resulting solution is evaporated to half volume and added with half volume of the same organic solvent. Evaporation and addition are repeated 1–4 times, preferably 2–3 times.

The last organic solvent aliquot is evaporated until 1/10–1/20 of the starting volume, thereafter a solvent selected from pyridine, picoline, lutidine in an amount ranging from 5 to 8 volumes, preferably from 6 to 7 volumes is added.

Step d

The mixture from step c) is cooled down to a temperature ranging from −50° C. to 10° C., preferably from −10° C. to 0° C. and the toluenesulfonyl halide or the alkanesulfonyl halide, preferably methanesulfonyl chloride, is slowly dropped thereto, under inert atmosphere, in an amount ranging from 1.0 to 3.0 equivalents, preferably from 1.5 to 2.0 equivalents (with respect to the starting 9,10-dihydrolysergic acid). The mixture is reacted until complete disappearance of D-6-n-propyl-8β-hydroxymethylergoline 4. After completion of the reaction compound 5, for example D-6-n-propyl-8β-mesyloxymethylergoline 5a, is precipitated by addition of 0.2–0.8 volumes of 15% ammonium hydroxide and 1–3 volumes of water; the product is filtered and washed with 5–10 volumes of deionized water. Compound 5a has a 98.5-99.0% purity, the main impurity being D-6-methyl-8β-mesyloxymethylergoline (HPLC percentage area 0.4–0.7%).

Humid compound 5 is dissolved in 20–50 volumes (with respect to the product volume), preferably 30–40 volumes, of an organic ester solvent, preferably methyl isobutyl ketone, ethyl acetate or n-butyl acetate, more preferably ethyl acetate. The resulting solution is evaporated to half volume and added with one volume of the same organic solvent. Evaporation and addition are repeated 1–4 times, preferably 2–3 times. The last aliquot of organic solvent is evaporated to 1/10–1/20 of the starting volume. A solvent selected from N-methylpyrrolidone, hexamethylphosphoramide, dimethylpropyleneurea and dimethylethyleneurea, in an amount ranging from 10 to 50 volumes, preferably 15–30 volumes with respect to compound 5, is added and the solution is further concentrated to remove the previous solvent.

Step e

The solution from step d) is added with 1–10 equivalents, preferably 2–4 equivalents, of solid sodium thiomethoxide, at a temperature ranging from –10° C. to 50° C., preferably from 0 to 5° C. The reaction is monitored by HPLC until complete disappearance of compound 5. After completion of the reaction (60–90' at 5° C.), the mixture is heated to 40–90° C., preferably 70–80° C., and added with 0.5–3 volumes, preferably 1–1.5 volumes of deionized water (with respect to the final volume of the reaction mixture): precipitation of pergolide 1 is observed. When the dropping is over the mixture is cooled to room temperature. The slurry is filtered and the losses in the mother liquor range from 0.5 to 1.5%. The product is dried at 40–70° C. for 10–30 hours. Compound 1 has a 99.8–99.9% purity; the major impurity is D-6-methyl-8β-methylthiomethylergoline (HPLC percentage area lower than 0.1%).

For the synthesis of pergolide mesylate 2, pergolide is mixed with 10–25 volumes of methanol, preferably with 12–15 volumes, or humid pergolide base is used. The solution is heated to 40–64° C., preferably to 50–60° C., and 1–1,1 equivalents of methanesulfonic acid are added. The solution is concentrated to half volume and one volume of a solvent selected for example from isopropanol, acetone and water, preferably isopropanol, is added and concentrated again to half volume. The mixture is cooled down to room temperature, filtered and dried under vacuum at 40–70° C. for 10–30 hours.

The quality of the resulting pergolide mesylate complies with the requirements of the European Pharmacopoeia.

The process of the present invention is particularly advantageous in that it can be carried out without isolating most of the intermediates. In particular, method A can be carried out without isolating the intermediates of formula 14, 12 and 4; this determines higher yields (higher than 80% compared with 9,10-dihydrolysergic acid) and higher safety. Moreover, the recovery of compound 5, which is remarkably more soluble compared with pergolide, allows to use less toxic solvents and to carry out a single chromatographic purification step on silica gel.

Method B is even more convenient, because it does not make recovery of intermediates 14 and 12 necessary and does not require cromatographic purification. In fact, hot-crystallization from water of compound 4 and pergolide 1 allows to significantly reduce the main impurities, in particular dihydrolysergol 8 which derives from the demethylation of compound 12. If not removed, compound 8 would co-precipitate and react in the subsequent steps, thus forming other impurities, such as those mentioned above.

A further advantage of the invention consists in that the demethylation of the quaternary salt 12 and the nucleophilic substitution which leads to pergolide can be carried out using a commercial sodium thiomethoxide solution, which does not have to be neutralized, as in Misner's procedure. According to Misner's procedure sodium thiomethoxide is prepared by dissolving methylmercaptan in the solvent (N-methylpyrrolidone) at low temperature (–10° C.) and subsequently salifying with NaOH; as an alternative, the commercial solution, pre-treated with methylmercaptan to remove excess of base, can be used.

A further advantage of the invention consists in that the demethylation of the quaternary salt 12 can also be conveniently carried out using the commercial 2-mercaptoethanol solution which, differently from sodium thiomethoxide, does not generate any toxic gas.

The process of the present invention is moreover particularly advantageous because it allows to obtain highly pure pergolide, sufficiently high not to require further purification of the derived salts (such as mesylate) in order to comply with the requirements of the European Pharmacopoeia.

The invention will be now illustrated in more detail by means of some examples.

EXAMPLES

Example 1

Step a), Method A and Method B: Conversion of 9,10-dihydrolysergic Acid 6 into D-6-methyl-6-n-propyl-8β-propyloxycarbonyl-6-ergolinium Iodide 14

In a multiple neck, round-bottom flask, 9.3 grams of 9,10-dihydrolysergic acid (0.0344 moles) are added under nitrogen atmosphere to 40 ml of N-methylpyrrolidone at room temperature, followed by 8.67 g of sodium bicarbonate (0.103 moles) and 30.4 g of n-propyl iodide (0.179 moles). The mixture is heated to 80° C. and reacted for about 10 hours.

The reaction can be monitored by HPLC using a C18 Hypersil column equipped with a 280 nm detector and eluted with 50:50 phosphate:acetonitrile buffer.

At the end of the reaction the starting product is completely converted into intermediate 14.

Example 2

Step b), Method A: Conversion of D-6-methyl-6-n-propyl 8β-propyloxycarbonyl-6-ergolinium Iodide 14 into D-6-methyl-6-n-propyl-8β-hydroxymethyl-6-ergolinium Iodide 12

The solution from example 1 is cooled down to 25° C., diluted with 120 ml of N-methylpyrrolidone and heated to 35° C. After addition of 5 g (0.0451 moles) of CaCl$_2$ and 6.5 g (0.172 moles) of NaBH$_4$, the mixture is heated at 45° C. for 1 hour. At the end of the reaction intermediate 14 is completely transformed into intermediate 12.

Step b), Method B: Conversion of D-6-methyl-6-n-propyl 8β-propyloxycarbonyl-6-ergolinium Iodide 14 into D-6-methyl-6-n-propyl-8β-hydroxymethyl-6-ergolinium Iodide 12

The solution from example 1 is cooled down to 45° C. and added of 5 g (0.0451 moles) of CaCl$_2$ and of 6.5 g (0.172 moles) of NaBH$_4$ dissolved in 45 ml of N-methylpyrrolidone. The mixture is heated at 55° C. for 1 hour. At the end of the reaction intermediate 14 is completely transformed into intermediate 12.

Example 3

Step c), Method A: Conversion of D-6-methyl-6-n-propyl-8β-hydroxymethyl-6-ergolinium Iodide 12 into D-6-n-propyl-8β-hydroxymethylergoline 4

The solution from example 2 is added with 185 ml of CH$_3$SNa (0.524 moles) in commercial 21% methanolic solution. The mixture is heated to 80° C. and reacted at the same temperature for about 3–4 hours distilling methanol off the reaction mixture.

The reaction can be monitored by HPLC using a C18 Hypersil column equipped with a 280 nm detector and eluted with 75:25 phosphate buffer: acetonitrile.

At the end of the reaction intermediate 12 is completely converted into D-6-n-propyl-8β-hydroxymethylergoline 4 (about 98%) and D-6-methyl-8,8-hydroxymethylergoline 8 (about 2%). The suspension is then concentrated under vacuum by means of a rotary evaporator until methanol is completely removed. The suspension is then added with 130 ml of deionized water. After addition of 300 ml of ethyl acetate, the mixture is stirred for 15–20 minutes, then the organic phase is separated. The aqueous phase is added with further 300 ml of ethyl acetate, stirred for 15–20 minutes and the organic phase is separated. The organic phases are pooled (total volume: about 600 ml) and washed twice with 600 ml of deionized water, then concentrated under vacuum to 30 ml with a rotary evaporator. Ethyl acetate (100 ml) is added and the solution is concentrated again to 30 ml. After addition of 100 ml of ethyl acetate and concentration to 15 ml, 100 ml of pyridine are added.

Step c), Method B

The solution from Example 2 is added with 20.6 g of NaOH (0.516 moles) and with 40.4 g of HO—CH$_2$CH$_2$—SH (0.516 moles), heated to 70° C. and reacted at 70° C. for about 7–10 hours.

The reaction can be monitored by HPLC using a C18 Hypersil column eluted with 75:25 phosphate buffer: acetonitrile equipped with a 280 nm detector.

At the end of the reaction intermediate 12 is completely transformed into D-6-n-propyl-8β-hydroymethylergoline 4 (about 98%) and dihydrolysergol 8 (about 2%).

The suspension is added with 30 ml of methanol and slowly added with 370 ml of 52 g/l disodium EDTA solution adjusted to pH 13 with NaOH, keeping the temperature at 70° C. NaCl (270 ml, 300 g/l) is then dropped thereto, keeping the temperature at 70° C., thereafter the mixture is slowly cooled down to 5° C. The product is filtered and washed first with 15 ml of 52 g/l disodium EDTA solution adjusted to pH 13 with NaOH, then with 100 ml of deionized water and dried in a static dryer under vacuum at 60° C. for 20 hours. 8.6 grams of dry product with 99% D-6-n-propyl-8β-hydroymethylergoline purity and with a D-6-methyl-8β-mesyloxymethylergoline content of 0.5% are obtained (other impurities: 0.5%). The humid D-6-n-propyl-8β-hydroymethylergoline 4 crystals are dissolved in 240 ml of ethyl acetate and the solution is concentrated under vacuum to 120 ml with a rotary evaporator. Ethyl acetate (120 ml) is added and the solution is concentrated again to 120 ml. After addition of a further 120 ml ethyl acetate aliquot, the solution is concentrated to 15 ml and added with 100 ml of pyridine.

Example 4

Step d), Method A: Conversion of D-6-n-propyl-8β-hydroxymethylergoline 4 into D-6-n-propyl-8β-mesyloxymethylergoline 5a The solution from example 3 is cooled down to −5° C. and 5.9 g (0.0515 moles) of methanesulfonyl chloride are slowly dropped thereto, keeping the temperature below 0° C. The mixture is reacted for 1 hour.

The reaction can be monitored by HPLC using a C18 Hypersil column equipped with a 280 nm detector and eluted with 50:50 phosphate buffer:acetonitrile.

At the end of the reaction the conversion of D-6-n-propyl-8β-hydroxymethylergoline 4 into D-6-n-propyl-8β-mesyloxymethylergoline 5a is complete. Once the reaction is completed 60 ml of 15% ammonium hydroxide and 190 ml of deionized water are added and the mixture is stirred for 15–20' and filtered. The product is washed on the filter with 100 ml of deionized water and dried in a static dryer under vacuum at 60° C. for 20 hours. 10.8 grams of dry product with 97% D-6-n-propyl-8β-mesyloxymethylergoline purity and 2% D-6-methyl-8β-mesyloxymethylergoline purity are obtained (other impurities: 1%).

Step d), Method B

The solution from Example 3 is cooled down to −5° C. and 5.9 g (0.0515 moles) of methanesulfonyl chloride are slowly dropped thereto, keeping the temperature below 0° C. The mixture is reacted for 1 hour.

The reaction can be monitored by HPLC with a C18 Hypersil column eluted with 50:50 phosphate buffer:acetonitrile equipped with a 280 nm detector.

At the end of the reaction, i.e. when D-6-n-propyl-8β-hydroxymethylergoline is completely transformed into D-6-n-propyl-8β-mesyloxymethylergoline, 60 ml of 15% ammonium hydroxide and 190 ml of deionized water are added. The mixture is stirred for 15–20' and filtered. The product is washed on the filter with 100 ml of deionized water and dried in a static dryer under vacuum at 60° C. for 20 hours. 10.5 Grams of dry product with 99% D-6-n-propyl-8β-mesyloxymethylergoline purity and 0.5% D-6-methyl-8β-mesyloxymethylergoline are obtained (other impurities 0.5%).

Example 5

Purification of
D-6-n-propyl-8β-mesyloxymethylergoline 5a,
Method A

The dry product obtained according to Example 4 (10.8 g) is dissolved in 100 ml of a 10:90 methanol:dichloromethane mixture. The solution is adsorbed over 500 g of silica gel conditioned with a 80:10:10 ethyl acetate:dichloromethane: methanol mixture and eluted with the same mixture. 20 Fractions 50 ml each are collected and analysed by HPLC; the fractions which contain pure 5a (A % HPLC>99.9%) are pooled, concentrated to 30 ml by means of a rotary evaporator and added with 220 ml of N-methylpyrrolidone.

Example 6

Step e) (Method A): Conversion of D-6-n-propyl-8 β-mesyloxymethylergoline 5a into Pergolide 1

The solution from example 5 is kept at 25° C. and added with 100 ml (0.284 moles) of CH3SNa in commercial 21% methanolic solution. The solution is concentrated by means of a rotary evaporator until methanol is completely removed. The reaction is monitored by HPLC using a C18 Hypersil column equipped with a 280 nm detector and eluted with 50:50 phosphate:acetonitrile buffer. At the end of the reaction compound 5a is completely converted into pergolide 1. Deionized water (350 ml) is added, the mixture is filtered and the product is washed with 100 ml of deionized water. The product is dried in a static dryer under vacuum at 60° C. for 20 hours. 8.64 grams of dry product with 99.9% D-6-n-propyl-8β-methylthiomethylergoline purity are obtained.

Step e) Method B

The humid crystals of D-6-n-propyl-8β-mesyloxymethylergoline 5a from example 4 are dissolved in 240 ml of ethyl acetate. The solution is concentrated under vacuum to 120 ml with a rotary evaporator. Ethyl acetate (120 ml) is added and the solution is concentrated again to 120 ml. After addition of a further 120 ml ethyl acetate aliquot, the solution is concentrated to 15 ml and added with 50 ml of N-methylpyrrolidone.

The resulting solution is kept at 0° C. and added with 4 g (0.058 moles) of solid CH₃SNa. The reaction is monitored by HPLC with a C18 Hypersil column equipped with a 280 nm detector and eluted with 50:50 phosphate buffer: acetonitrile At the end of the reaction compound 5a is completely transformed into pergolide 1. N-methylpyrrolidone (170 ml) is added and the solution is heated to 75° C. Deionized water (286 ml) is dropped thereto, keeping the temperature at 75° C., then the mixture is cooled to room temperature and filtered. The product is washed with 100 ml of deionized water at 75° C. The product is dried in a static dryer under vacuum at 60° C. for 20 hours. 8.4 grams of dry product with 99.8% D-6-n-propyl-8β-methylthiomethylergoline purity and 0.1% D-6-methyl-8β-methylthiomethylergoline purity are obtained.

Example 7

Salification of Pergolide 1 into Pergolide Mesylate
2 (Method A and B)

8.64 grams (0.0275 moles) of pergolide 1 from example 6 are suspended in 130 ml of methanol at room temperature. The suspension is heated to 60° C. and added with 2.70 grams (0.0281 moles) of methanesulfonic acid in 15% methanolic solution. The resulting solution is evaporated to 55 ml, added with 60 ml of isopropanol and concentrated again to 55 ml. The mixture is allowed to cool down to 25° C. and filtered. The crystal product on the filter is washed twice with 50 ml of isopropanol. The product is dried in a static dryer under vacuum at 60° C. for 24 hours.

10.45 grams of pergolide mesylate 2 with quality complying with the European Pharmacopoeia standards (EP suppl. 2001) are obtained (molar yield from 9,10-dihydrolysergic acid to pure pergolide mesylate: 74%).

The invention claimed is:
1. A process for the synthesis of pergolide 1

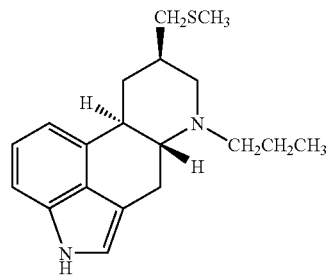

comprising the following steps:
a) reaction of 9,10-dihydrolysergic acid 6

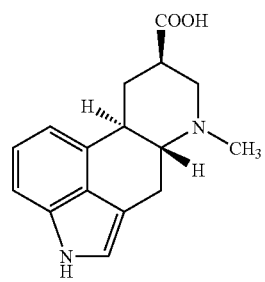

with propyl iodide to give D-6-methyl-6-n-propyl-8(3-propyloxycarbonyl-6-ergolinium iodide 14;

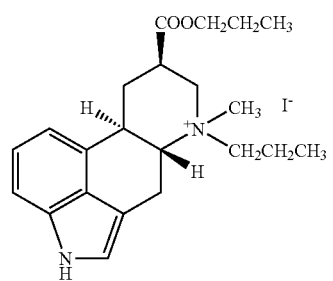

b) reduction of intermediate 14 to give D-6-methyl-6-n-propyl-8(3-hydroxymethyl-6-ergolinium iodide 12;

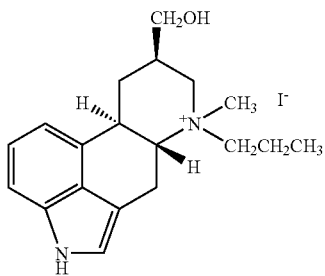

c) demethylation of intermediate 12 with nucleophiles to give D-6-n-propyl-8(3-hydroxymethylergoline 4;

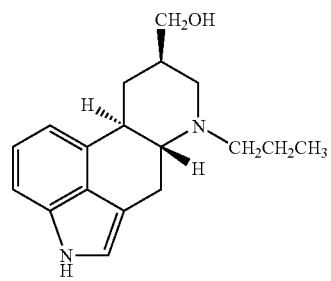

d) reaction of D-6-n-propyl-8p-hydroxymethylergoline 4 with an alkylsulfonyl halide or a toluenesulfonyl halide RS02X, in which R is a straight or branched Cl—C alkyl chain, or a C6H5CH2 residue, whereas X is a halogen selected from fluorine, chlorine, bromine and iodine
to give D-6-n-propyl-8p-alkylsulfonyloxymethylergoline or D-6-npropyl-8(3-tosyloxymethylergoline 5, in which R has the meanings defined above;

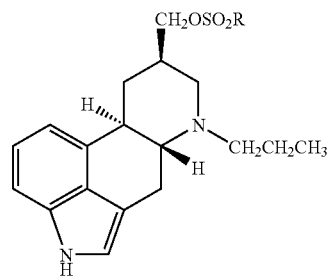

e) reaction of compound of formula 5 with sodium thiomethoxide to give pergolide 1.

2. A process as claimed in claim 1) in which steps b), c) and d) are carried out without recovering intermediates 14, 12 and 4.

3. A process as claimed in claim 1) in which compounds 4, 5 and 1 are recovered by crystallization.

4. A process as claimed in claim 3) in which steps b) and c) are carried out without recovering intermediates 14 and 12.

5. A process as claimed in claim 1 in which before step e) the compound 5 is purified by chromatography.

6. A process according to claim 1 in which the reduction of step b) is carried out with metal hydrides.

7. A process as claimed in claim 6) in which the metal hydride is sodium borohydride.

8. A process according to claim 1 in which the demethylation of step c) is carried out with alkaline thioalkoxides.

9. A process as claimed in claim 8) in which alkaline thioalkoxides are sodium, potassium or lithium thioalkoxides.

10. A process as claimed in claim 9) in which the thioalkoxide is sodium thiomethoxide.

11. A process as claimed in claim 9) in which the thioalkoxide is sodium 2-mercaptoethoxide.

12. A process as claimed in claim 1 in which the alkylsulfonyl halide is methanesulfonyl chloride.

13. A process as claimed in claim 3 in which compound 4 from step c) is recovered from the reaction mixture by crystallization with an EDTA aqueous solution and an alkaline or alkaline-earth metal chloride aqueous solution at a temperature ranging from 60 to 90° C.

14. A process as claimed in claim 3) in which pergolide 1 from step e) is recovered from the reaction mixture by crystallization with water at a temperature ranging from 40 to 90° C.

15. The quaternary salt of formula 14

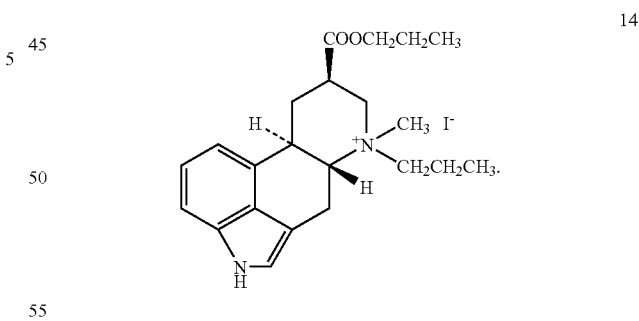

* * * * *